United States Patent [19]

Breen et al.

[11] Patent Number: 4,727,051
[45] Date of Patent: Feb. 23, 1988

[54] PRODUCTION OF HALIDE-AND ALKOXY-CONTAINING MAGNESIUM COMPOSITIONS

[75] Inventors: Michael J. Breen; Dennis B. Malpass, both of LaPorte, Tex.

[73] Assignee: Stauffer Chemical Company, Westport, Conn.

[21] Appl. No.: 941,673

[22] Filed: Dec. 15, 1986

[51] Int. Cl.$^4$ .............................................. B01J 31/02
[52] U.S. Cl. ................................... 502/171; 502/120; 502/126; 502/134; 568/851
[58] Field of Search ............... 502/134, 120, 126, 111, 502/171; 568/851

[56] References Cited

U.S. PATENT DOCUMENTS

| | | | |
|---|---|---|---|
| 3,737,393 | 6/1973 | deVries | 252/431 R |
| 4,127,507 | 11/1978 | Fannin et al. | 252/431 R |
| 4,207,207 | 6/1980 | Sanchez et al. | 252/431 R |
| 4,209,602 | 6/1980 | Kuroda et al. | 526/114 |
| 4,220,554 | 9/1980 | Scata et al. | 502/134 X |
| 4,222,969 | 9/1980 | Fannin et al. | 260/665 R |
| 4,370,257 | 1/1983 | Imai et al. | 502/134 X |
| 4,455,387 | 6/1984 | McKinnie et al. | 502/153 |
| 4,525,554 | 6/1985 | Tanaka et al. | 502/134 X |

OTHER PUBLICATIONS

Turova et al., "Alkoxymagnesium Halides", J. Organometal. Chem., 42:9-17 (1972).
Turova et al., "Alkoxymagnesium Chlorides", Bull. of the Acad. of Sciences of the USSR, 186:358-361 (1969).
Turova et al., "Interaction of Magnesium Chloride and Alcoholates", Bulletin of the Academy of Sciences of the USSR, 173(2):374-377 (1967).
Yabroff et al., "The Preparation and Properties of Tertiary Butyl Phenylacetae", J.A.C.S., 54:2453-2455 (1932).

Primary Examiner—Patrick P. Garvin
Attorney, Agent, or Firm—Joel G. Ackerman

[57] ABSTRACT

Compositions having the formula $$X_nMg(OR)_{2-n}$$

in which X is chloro, bromo or iodo; R is a $C_1-C_{10}$ alkyl group and n is a value from about 0.2 to about 1.9 are produced by a process comprising preparing an alkanol adduct of a magneisum halide, reacting the product of this step with metallic magnesium, and drying the product. The compositions are useful as olefin polymerization catalyst components and supports.

13 Claims, No Drawings

PRODUCTION OF HALIDE-AND ALKOXY-CONTAINING MAGNESIUM COMPOSITIONS

This invention pertains to the production of magnesium compositions having the formula $$X_nMg(OR)_{2-n}$$

in which X is chloro, bromo, or iodo; R is a $C_1$-$C_{10}$, preferably $C_1$-$C_6$ alkyl group; and n is a value from about 0.2 to about 1.9.

Some compositions of this type, such as alkoxymagnesium halides, have been found useful as olefin polymerization catalyst supports or components. See, for instance, U.S. Pat. No. 4,209,602. In general, these types of compositions have been prepared by two processes.

In one process, a Grignard reagent is reacted with a lower alkanol, with an ether, such as diethyl ether, present during the reaction. See, for instance, Yabroff et al., *J.A.C.S.*, Vol. 54, 2453 (1932). However, it was later established, for instance by Turova et al., *Bulletin of the Academy of Sciences of the USSR* (Doklady Aladem ii Nauk SSSR), Vol. 173, No. 2, pp. 374-377 (1967), that such processes do not in fact form the desired product but instead produce some type of complex.

The work by Turova et al., supra, and also described in a second article [ibid., Vol. 186, pp. 358-361 (1969)], shows that alkoxymagnesium halides can be produced by first reacting an adduct having the formula $MgX_2 \cdot 6ROH$ (in which X is a halogen and R is an aklyl group) with a magnesium alkoxide to form what is termed a Sorel "cement", which is then decomposed at temperatures of 160° C. and above, preferably under vacuum, to produce the desired alkoxymagnesium halide. Such cements, however, are somewhat difficult to work with, and are not necessarily uniform in composition, either chemical or physical. They are difficult to handle on a commerical scale.

SUMMARY OF THE INVENTION

This invention comprises a process for the production of halide- and alkoxy-containing magnesium compositions having the formula $$X_nMg(OR)_{2-n}$$

in which X is chloro, bromo, or iodo; R is an $C_1$-$C_{10}$ alkyl group; and n is a value from about 1 to about 1.9, comprising (a) preparing an adduct of a magnesium halide having the formula $MgX_2$ with an alkanol having the formula ROH;

(b) reacting the product of step (a) with metallic magnesium; and (c) drying the product of step (b) at an elevated temperature.

DETAILED DESCRIPTION OF THE INVENTION

According to this invention, such halide- and alkoxy-containing magnesium compositions are produced in a new manner which is readily suitable for operation on a commercial scale and obviates some of the disadvantages of the prior art processes.

The products of the present process have the empirical formula $$X_nMg(OR)_{2-n}$$

in which X is a halogen, that is, chlorine, bromine or iodine; R is a $C_1$-$C_{10}$, preferably $C_1$-$C_6$, alkyl group (straight or branched chain); and n is a number from about 0.2 to about 1.9. Most preferably, X is chlorine, R is methyl or ethyl and n is about 1. These compositions may be discrete complexes characterized by the above formula, or they may also contain magnesium halides and/or alkoxides.

The first step of this process involves the preparation of a $C_1$-$C_{10}$ alkanol adduct of a magnesium halide. In general, this is preferably accomplished by reaction of a magnesium halide composition with a lower alkanol having the formula ROH, in which R is $C_1$-$C_{10}$ alkyl. Suitable alkanols include methanol, ethanol, n-hexanol and 2-ethylhexanol.

The magnesium halide composition preferably comprises magnesium chloride but may also comprise other magnesium halides, such as magnesium bromide or iodide. This composition may be in the form of technical or reagent grade magnesium halide, but in the preferred embodiment of this process comprises the magnesium halide—(preferably magnesium chloride—) containing product precipitated during the production of organomagnesium compounds by reaction of magnesium metal with alkyl halides. Processes of this type are described in a number of patents, for instance, U.S. Pat. Nos. 3,737,393, 4,127,507, 4,207,207, 4,222,969 and 4,455,387. In such processes, one or more alkyl halides are reacted with metallic magnesium to produce a compound which is a dialkylmagnesium. A by-product of this reaction is the corresponding magnesium halide (such as magnesium chloride) which precipitates out as a solid and is removed from the process. The magnesium halide solids removed from this process will also contain varying amounts of other materials, such as solvents used in the reaction, unreacted alkyl halide, unreacted metallic magnesium, organomagnesium product etc. Depending on the point at which the magnesium halide-containing solids are separated from the dialkylmagnesium products, the magnesium halide composition may also contain other ingredients such as various viscosity reducing agents (as mentioned in the above patents, for instance). Such ingredients are not generally deemed detrimental to our process, however, and magnesium halide solids recovered from such an organomagnesium process may be used without requiring separation of the magnesium halide from the remaining ingredients.

Typical magnesium halide solids compositions will generally be in the form of a slurry in the solvent used in the organomagnesium production process (for instance, n-heptane) containing generally 30-50 weight percent solids. The solids will generally comprise (by weight) about 90-95% magnesium halide, about 3-7% metallic magnesium, about 3-6% dialkylmagnesium, and about 1-2% oxygenated magnesium compounds.

The reaction of a magnesium halide with the lower alkanol is an exothermic reaction and thus may be initiated at or near room temperature. The mole ratio of magnesium halide to alkanol may range from about 1 to about 10, and is preferably about 3-6.

Solvents such as n-heptane, n-hexane or toluene are advantageous in this step in order to permit the reaction of the alkanol and magnesium halide without the occurrence of any substantial agglomeration.

When the process involves the reaction of technical or reagent grade magnesium halide with an alkanol, the alkanol adduct is produced directly by such reaction; the amount of alkanol in the adduct, of course, will depend on the ratio of alkanol to magnesium halide in this step.

When the magnesium halide composition is a magnesium halide product precipitated during the production of organomagnesium compounds by reaction of magnesium with alkyl halides, the composition will, as mentioned above, contain some metallic magnesium (generally about 3–7% by weight). When such a composition is contacted with the alkanol, to produce the magnesium halide alkanol adduct, alkyl magnesiums and metallic magnesium will also react with the alkanol to produce a magnesium alkoxide. If the temperature of this step has reached an undesirably high level, the adduct or reaction product may be cooled before proceeding to the next step. However, cooling is not necessary in many embodiments of this process. The resulting first step product may be used in toto in the second stage. However, it may be desirable to first purify the magnesium halide alkanol adduct before carrying out the second stage of this process in order to produce a purer product or one which has an optimum particle size.

Thus, when such magnesium halide compositions are used in the process of this invention, an additional step is recommended. This step involves the treatment of the material with a halide source. The halide source can be a halogen (e.g. chlorine, bromine or iodine), a hydrohalide acid (e.g., hydrochloric acid), a tetrahalide, preferably a silicon tetrahalide such as silicon tetrachloride, or an organoaluminum halide such as ethylaluminum dichloride. The halide source may be added prior or to subsequent to the addition of the alkanol. When added prior to the introduction of alkanol the halide source serves to chlorinate the residual dialkylmagnesium. When added after the alkanol, the halide source reacts with magnesium alkoxide to produce the magnesium halide alkanol adduct.

In such case, the magnesium halide alkanol adduct may be appropriately recrystallized from a solvent (such as the solvent employed in carrying out the first step of this process) and filtered, or obtained in a solid form by azeotropically removing alkanol and solvent at temperatures not exceeding 120° C.

Magnesium halide adducts of higher alkanols such as those having 6 or more carbon atoms can be prepared by direct reaction of the magnesium halide product with the appropriate alkanol or by first reacting the magnesium halide with a lower alkanol such as ethanol to prepare the magnesium-lower alkanol adduct, followed by replacement of the lower alkanol by reaction of the adduct with the higher alkanol. Particularly when employing a magnesium halide composition obtained from the production of organomagnesium compounds as a starting material for this process, the optimum way to produce the higher alkanol adducts is by a combination of production of the lower alkanol, (e.g., ethanol) adduct, (including chlorination of the magnesium alkoxides), followed by replacement of the ethanol or lower alkanol by a higher molecular weight alkanol.

In the second step of this process, the magnesium halide alkanol adduct is reacted with metallic magnesium. This reaction is conducted at a temperature from about 60° to about 120° C., preferably from about 70° to about 80° C. The metallic magnesium may be in any convenient form, and need not be activated for use in this process. The amount of magnesium employed in this step is controlled in order to obtain the desired ratio of halogen to magnesium.

Subsequent to the second step, any excess alkanol or other volatiles (such as solvent contained in the magnesium halide composition) are distilled off, and the remaining solids are dried. The drying temperature is preferably at least above 120° C. and most preferably about 160° C. Drying at 120° C. or below will generally result in an ethanol adduct of the desired magnesium-containing composition having about 1 equivalent of ethanol per equivalent of magnesium. Drying at a higher temperature will result in the desired product.

The value of n in the halide-containing product compositions may range from about 0.2 to about 1.9, depending on the stoichiometry employed. Preferably the value of n is from about 0.3 to about 1.1, most preferably about 1. This process is thus capable of producing compositions in which n is about 1.75 or 1.80 and are therefore relatively high in halide as opposed to alkoxide content, as disclosed in Turova (1969).

Operation according to the present process not only produces a good yield of the desired product, but does not require passing through a "cement" product and thus eliminates the solids handling problem associated with that type of product.

The following represent examples of the conduct of the process according to the present invention.

EXAMPLE 1

This example utilized as a magnesium halide composition a slurry obtained from the production of a solution of n-butylethylmagnesium in n-heptane by the reaction of n-butyl and ethyl chlorides with magnesium in heptane as described in U.S. Pat. No. 4,127,507. This composition contained magnesium chloride (99.8 g, 1.05 moles), n-heptane and a small amount of n-butylethylmagnesium residual material. To this composition there was added 369.3 g (8.03 moles) of ethanol, at a rate sufficient to maintain a pot temperature of 70° C.

The reaction was conducted for 1 hour. Then the reactor was cooled to 25° C., charged with 16.3 g (0.679 mole) metallic magnesium and heated to 70° C. for one hour. At the end of this period, the n-heptane and residual ethanol were distilled off from the solids, and the solids dried at 160° C. under flowing nitrogen. A yield of 193 grams of an off-white powdered solid was obtained. For the product the following values were determined: magnesium—calculated—22.95%, found—23.1% chlorine—calculated—33.97%, found—34.2%. The value of n was about 1.

EXAMPLE 2

This example demonstrates the production of a magnesium chlorideethanol adduct using as the magnesium halide source a slurry similar to that employed in Example 1, with chlorination of magnesium alkoxide formed from magnesium metal in said slurry.

The magnesium halide source comprised 71.0 g of a slurry obtained from a process as in Example 1. This slurry contained 50 weight percent solids, including 4.4 weight percent butylethylmagnesium. To the slurry was added 7.2 g (5.0 ml) silicon tetrachloride. The slurry was then stirred at room temperature for 10 minutes. Then, about 9 molar equivalents ethanol was added slowly over 1.5 hours in order to maintain the temperature of the reaction under reasonable control.

The flask temperature rose to 60° C. during this time. A second portion of 7.2 g silicon tetrachloride was added. The solution was hot filtered, then added to 1 liter of stirred heptane to precipitate the solid magnesium chloride ethanol adduct: $MgCl_2.6C_2H_5OH$. After filtering and washing about 140 g of this solid was obtained as a white microcrystalline material. A portion of this solid was mixed with heptane, heated to 120° C. and vacuum dried at the same temperature. Analysis showed 20.57% Mg, 58.97% Cl with a chlorine/magnesium ratio of 1.97, which corresponds to $MgCl_2.0.5C_2H_5OH$.

EXAMPLE 3

This example illustrates the production of a higher alkanol magnesium halide adduct.

To a sample (50 g, 0.134 mole) of magnesium chloride ethanol adduct prepared as in Example 2 and having an ethanol:magnesium chloride ratio of 6 was added 60 ml of 2-ethyl-1-hexanol. The solution was then distilled at 120° C. to remove ethanol and heptane. Decane (97.7 g) was added to the resulting viscous solution to obtain the magnesium chloride-2-ethylhexanol adduct as a clear, colorless solution. It had a molar ratio of 2-ethylhexanol:magnesium chloride of 2.9 and still contained approximately 1% ethanol.

EXAMPLE 4

This example demonstrates the preparation of a hexoxymagnesium chloride.

A sample of the slurry described in paragraph 1 of Example 1 was filtered, washed with hexane, then vacuum-dried. Five grams of this solid, 100 ml heptane, and 40 ml n-hexanol was added to a flask and heated at 95° C. for 30 minutes. Magnesium metal (0.41 g, 0.017 mole) and a small quantity of iodine (as an initiator) were added. The solution was heated to 180° C. to distill out n-hexanol and heptane, then solids were vacuum dried at 180° C. to dryness. For the product the following values were determined: magnesium—calculated—15.1%, found—15.7%; chlorine—calculated—22.1%, found—21.7%. The value of n was about 0.95.

EXAMPLE 5

This example illustrates the use of a halide- and alkoxy-containing magnesium composition prepared according to this invention as a support for a titanium-containing catalyst in the slurry polymerization of ethylene.

There were introduced into a flask 10.1 g (0.096 mole) of a magnesium composition prepared as in Example 3 (n=1.0), 50 ml hexane and 18.3 g (0.096 mole) titanium tetrachloride. The suspension was stirred for 1 hour at 70° C. The solids were filtered, washed twice with n-hexane and vacuum dried. A pale yellow flowable powder was obtained which contained 2.30% titanium.

The above titanium-containing material was employed as a polymerization catalyst for ethylene according to the following procedure: A 4 liter reactor was partially filled with hexane which was stirred at 1000 rpm. Reactants were used in the amounts indicated in the following table. The reactants were added to the hexane in the order triisobutylaluminum (TIBAL), catalyst, hydrogen (40 psig charged at 50° C.) and ethylene (150 psig). The polymerization was conducted for a period of 1 hour, after which the reactor was vented, the product filtered and vacuum dried. The following Table 1 sets out the results which were obtained. The amount of TIBAL is expressed as a molar ratio of aluminum to titanium. Productivity is expressed as grams polymer per gram of catalyst; specific activity as $kgPE.gTi^{-1}.atm\ C_2H_4^{-1}\ hr^{-1}$. MI=Melt Index (ASTM method D-1238, Condition E at 190° C., 2160 gram load; expressed as grams per 10 minutes). MIR=Melt Index Ratio, expressed as the ratio of the High Load Melt Index (HLMI) to MI. (HLMI obtained under same conditions as MI except with 21,600 gram load, Condition F).

TABLE 1

| Run | Catalyst Weight | Al/Ti | Temp (°C.) | Productivity | Specific Activity | MI | MIR |
|---|---|---|---|---|---|---|---|
| A | 130 mg | 130 | 89 ± 4 | 4200 | 24.1 | 5.0 | 33 |
| B | 40 mg | 400 | 86 ± 2 | 8500 | 49.3 | 1.4 | 32 |

EXAMPLE 6

This example illustrates the use of a composition according to this invention as a polymerization catalyst component.

A treated silica support was prepared as follows: silica (Davidson grade #952), calcined at 600° C. for 18 hours, was treated with 5 weight % triethylaluminum in n-heptane for 2 hours at 60° C., filtered, washed with hexane, and vacuum dried.

The treated silica (10 g) was mixed with 50 ml tetrahydrofuran, 0.855 g (0.0045 mole) titanium tetrachloride and 1.0 g (0.0096 mole) of the halide- and alkoxy-containing magnesium composition used in Example 5, under a nitrogen atmosphere. The mixture was heated for 3 hours at 60° C. with stirring. Solvent was removed by purging with nitrogen and vacuum drying. There was isolated 12.8 g of a dry flowable powder which contained 1.78% titanium.

The catalyst thus obtained was employed in polymerization of ethylene according to the procedure of Example 5 except that the time was 90 minutes. The results are set out below in Table 2.

TABLE 2

| Run | Catalyst Weight | Al/Ti | Temp (°C.) | Productivity | Specific Activity | MI | MIR |
|---|---|---|---|---|---|---|---|
| C | 148 mg | 108 | 85 ± 1 | 1220 | 6.1 | 0.3 | 39 |
| C | 174 mg | 103 | 85 ± 1 | 980 | 4.9 | 0.3 | 45 |

Olefin polymerization catalyst systems containing compositions according to this invention as catalyst components will contain a titanium halide catalyst and optionally an aluminum containing co-catalyst. The titanium content will comprise about 0.1-5% by weight of the catalyst system, preferably 0.4-2.0% by weight. The mole ratio of magnesium composition (invention) to titanium will be 0.5:1-10:1, preferably 2:1-4:1.

What is claimed is:

1. A process for the production of a halide- and alkoxy-containing magnesium composition having the formula $$X_nMg(OR)_{2-n}$$

in which X is chloro, bromo, or iodo; R is a $C_1-C_{10}$ alkyl group; and n is a value from about 0.2 to about 1.9 comprising:

(a) preparing an adduct of a magnesium halide having the formula $MgX_2$ with an alkanol having the formula ROH;

(b) reacting the product of step (a) with metallic magnesium; and (c) drying the product of step (b) to obtain a halide- and alkoxy-containing magnesium composition.

2. A process according to claim 1 in which X is chloro.

3. A process according to claim 1 in which n is about 1.

4. A process according to claim 1 in which R is a $C_1$-$C_6$ alkyl group.

5. A process according to claim 1 in which R is methyl or ethyl.

6. A process according to claim 1 in which step (a) comprises reacting a magnesium halide composition with an alkanol having the formula ROH.

7. A process according to claim 6 in which the magnesium halide composition comprises a solid magnesium halide recovered as by-product from a process for the production of dialkylmagnesium compounds by reaction of metallic magnesium with one or more alkyl halides.

8. A process according to claim 7 further comprising isolating the magnesium halide-alkanol adduct from the product of step (a).

9. A process according to claim 7 further comprising treating the magnesium halide composition with a halogenating agent either prior or subsequent to reacting it with the alkanol.

10. A process according to claim 7 in which an adduct of a $C_1$-$C_4$ alkanol is prepared in step (a), further comprising reacting said $C_1$-$C_4$ alkanol adduct with a $C_6$-$C_{10}$ alkanol to obtain a $C_6$-$C_{10}$ alkanol adduct of the magnesium halide.

11. A process according to claim 6 in which an adduct of a $C_1$-$C_4$ alkanol is prepared in step (a), further comprising reacting said $C_1$-$C_4$ alkanol adduct with a $C_6$-$C_{10}$ alkanol to obtain a $C_6$-$C_{10}$ alkanol adduct of the magnesium halide.

12. A process according to claim 1 in which step (c) is conducted at a temperature of at least above 120° C.

13. A process according to claim 1 in which step (b) is conducted at a temperature of from about 60 to about 120° C.

* * * * *

UNITED STATES PATENT AND TRADEMARK OFFICE
CERTIFICATE OF CORRECTION

PATENT NO. : 4,727,051
DATED : February 23, 1988
INVENTOR(S) : Michael J. Breen et al.

It is certified that error appears in the above-identified patent and that said Letters Patent is hereby corrected as shown below:

Page 1, Assignee: "Stauffer Chemical Company, Westport, Conn." should read -- Texas Alkyls, Inc., Deer Park, Texas --.

Signed and Sealed this

Thirtieth Day of August, 1988

Attest:

DONALD J. QUIGG

Attesting Officer

Commissioner of Patents and Trademarks